US012797418B2

(12) United States Patent
Liu et al.

(10) Patent No.: US 12,797,418 B2
(45) Date of Patent: Nov. 17, 2026

(54) HUMAN INDUCED PLURIPOTENT STEM CELLS-DIFFERENTIATED CARDIOMYOCYTES, METHODS OF PRODUCING THE SAME, AND USES THEREOF IN TREATING CARDIAC DISEASES

(71) Applicant: NATIONAL CHENG KUNG UNIVERSITY, Tainan City (TW)

(72) Inventors: Yen-Wen Liu, Tainan City (TW); Yan-Shen Shan, Tainan City (TW)

(73) Assignee: NATIONAL CHENG KUNG UNIVERSITY, Tainan City (TW)

( * ) Notice: Subject to any disclaimer, the term of this patent is extended or adjusted under 35 U.S.C. 154(b) by 649 days.

(21) Appl. No.: 18/353,885

(22) Filed: Jul. 18, 2023

(65) Prior Publication Data

US 2025/0025512 A1 Jan. 23, 2025

(51) Int. Cl.

| | |
|---|---|
| ***A61K 35/34*** | (2015.01) |
| ***A61P 9/10*** | (2006.01) |
| ***C12N 5/077*** | (2010.01) |
| ***C12N 9/22*** | (2006.01) |
| ***C12N 15/11*** | (2006.01) |
| ***C12N 15/90*** | (2006.01) |

(52) U.S. Cl.

CPC ................ *A61K 35/34* (2013.01); *A61P 9/10* (2018.01); *C12N 5/0657* (2013.01); *C12N 9/22* (2013.01); *C12N 15/11* (2013.01); *C12N 15/907* (2013.01); *C12N 2310/20* (2017.05); *C12N 2500/32* (2013.01); *C12N 2500/38* (2013.01); *C12N 2501/30* (2013.01); *C12N 2501/415* (2013.01); *C12N 2506/45* (2013.01); *C12N 2800/80* (2013.01)

(58) Field of Classification Search

CPC ..... C12N 5/0657; C12N 2506/45; C12N 5/10
See application file for complete search history.

(56) References Cited

U.S. PATENT DOCUMENTS

2024/0226178 A1* 7/2024 Murry .................... C12N 15/11

OTHER PUBLICATIONS

Hermann (British Journal of Pharmacology (2012)166501-509).*

* cited by examiner

*Primary Examiner* — Valarie E Bertoglio
(74) *Attorney, Agent, or Firm* — NZ Carr Law Office

(57) ABSTRACT

Disclosed herein is an isolated population of cardiomyocytes differentiated from human induced pluripotent stem cells (hiPSCs), wherein the isolated population of cardiomyocytes comprises genomic deletions in HCN1 and HCN4 genes. According to some embodiments of the present disclosure, the isolated population of cardiomyocytes further comprises genomic deletions in HCN2 and HCN3 genes. Also disclosed herein are methods of producing the isolated population of cardiomyocytes, and methods of treating subjects suffering from cardiac diseases by administering the isolated population of cardiomyocytes to the subjects.

2 Claims, 1 Drawing Sheet

Specification includes a Sequence Listing.

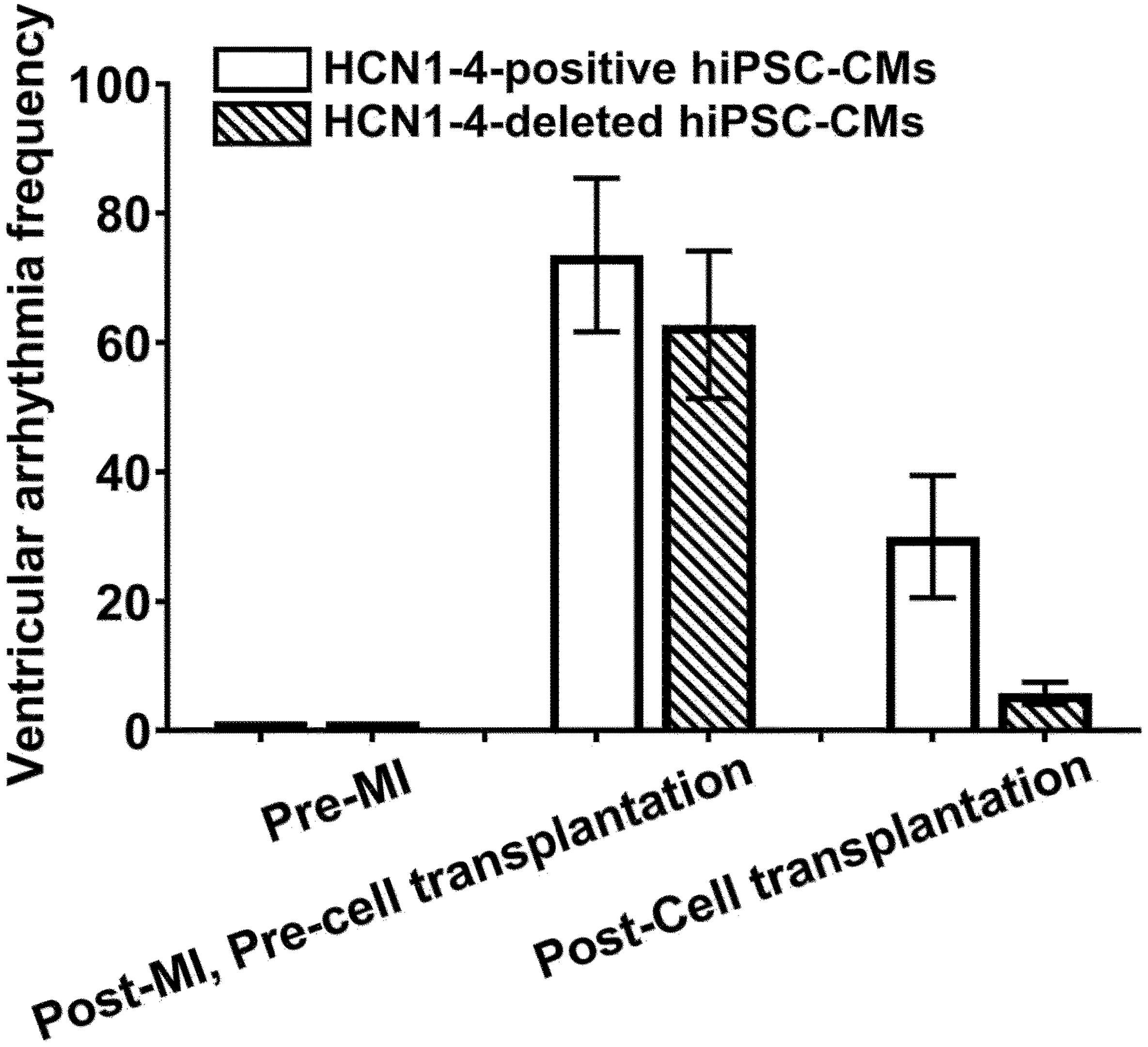
HCN1-4-positive hiPSC-CMs
HCN1-4-deleted hiPSC-CMs
Ventricular arrhythmia frequency
100
80
60
40
20
0
Pre-MI
Post-MI, Pre-cell transplantation
Post-Cell transplantation

HUMAN INDUCED PLURIPOTENT STEM CELLS-DIFFERENTIATED CARDIOMYOCYTES, METHODS OF PRODUCING THE SAME, AND USES THEREOF IN TREATING CARDIAC DISEASES

The present application is being filed along with a Sequence Listing XML in electronic format. The Sequence Listing XML is provided as a XML file entitled AJ23014N_Sequence_Listing, created Jul. 5, 2023, which is 32 Kb in size. The information in the electronic format of the Sequence Listing XML is incorporated herein by reference in its entirety.

BACKGROUND OF THE INVENTION

1. Field of the Invention

The present disclosure in general relates to the field of disease treatment. More particularly, the present disclosure relates to a population of human induced pluripotent stem cells (hiPSCs)-differentiated cardiomyocytes and uses thereof in treating cardiac diseases.

2. Description of Related Art

Cardiac disease is one of leading causes of death globally. It refers to several types of heart conditions, including coronary heart disease, myocardial infarction, cardiac arrhythmia, myocardial ischemia, and cardiac failure. According to the Centers for Disease Control and Prevention (CDC), about 695,000 people in the United States died from cardiac disease in 2021, i.e., one in every five deaths. A major reason of the high mortality rate of cardiac disease is that the heart is one of the least regenerative organs in the body; when damage occurs to the myocardium, cardiomyocytes (native cardiac muscle cells), are replaced with fibrotic scar tissue, a pathophysiologic process known as "cardiac fibrosis" that leads to cardiac dysfunction and heart failure subsequently.

Over the past 20 years, there have been extensive efforts to induce the heart to heal by muscle regeneration rather than scarring. It is reported that cardiomyocytes can be derived from human pluripotent stem cells (hPSCs), such as human embryonic stem cell (hESC) or human induced pluripotent stem cells (hiPSC). The hPSC-derived cardiomyocytes survive after transplantation and form new, maturing myocardium in animal models of myocardial infarction. However, some animals experienced graft-associated ventricular arrhythmias, including ventricular tachycardia and accelerated idioventricular rhythm (AIVR).

In view of the forging, there exists in the related art a need for an improved method for treating cardiac disease without causing adverse effect, e.g., ventricular arrhythmias.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to an isolated population of cardiomyocytes. According to the embodiments of the present disclosure, the isolated population of cardiomyocytes is differentiated from human induced pluripotent stem cells (hiPSCs).

According to some embodiments, the isolated population of cardiomyocytes comprises genomic deletions in HCN1 and HCN4 genes, and accordingly, does not express hyperpolarization-activated cyclic nucleotide gated potassium channel (HCN) 1 and HCN4. According to some embodiments, in addition to HCN1 and HCN4 genes, the isolated population of cardiomyocytes further comprises genomic deletions in HCN2 and HCN3 genes; in the embodiments, the isolated population of cardiomyocytes does not express HCN1, HCN2, HCN3 and HCN4.

Also disclosed herein is a method of producing the isolated population of cardiomyocytes of the present disclosure. The method comprises, (a) making deletions in the HCN1 and HCN4 genes of the hiPSCs; and
(b) incubating the hiPSCs of step (a) in a differentiation medium to induce differentiation of the hiPSCs into the population of cardiomyocytes.

According to certain embodiments, the method further comprises making deletions in the HCN2 and HCN3 genes of the hiPSCs prior to step (b).

Another aspect of the present disclosure pertains to a method of treating a cardiac disease in a subject. The method comprises administering to the subject an effective amount of the isolated population of cardiomyocytes of the present disclosure, so as to ameliorate or alleviate the symptoms of the cardiac disease.

According to some embodiments, the isolated population of cardiomyocytes is intramyocardially administered to the subject. In some exemplary embodiments, the isolated population of cardiomyocytes is administered to the left ventricle of the heart of the subject.

Depending on desired purposes, the cardiac disease may be myocardial infarction, cardiac arrhythmia, myocardial ischemia, cardiac failure, angina pectoris, or a combination thereof.

The subject is a mammal; preferably, a human.

Many of the attendant features and advantages of the present disclosure will become better understood with reference to the following detailed description considered in connection with the accompanying drawings.

BRIEF DESCRIPTION OF THE DRAWINGS

The present description will be better understood from the following detailed description read in light of the accompanying drawings, where:

FIG. 1 is a histogram depicting the effect of the present HCN-deleted hiPSC-CMs on inhibiting post-transplant ventricular arrhythmias according to Example 2 of the present disclosure. HCN1-4-positive hiPSC-CMs: cardiomyocytes derived from hiPSC expressing HCN1, HCN2, HCN3 and HCN4 genes; HCN1-4-deleted hiPSC-CMs: cardiomyocytes derived from the $HCN1^{-}/HCN2^{-}/HCN3^{-}/HCN4^{-}$ hiPSCs. Pre-MI: ventricular arrhythmia frequency of animals prior to myocardial infarction (ischemia-reperfusion, I-R) surgery; Post-MI, Pre-cell transplantation: ventricular arrhythmia frequency of animals after myocardial infarction surgery and prior to hiPSC-CM transplantation; Post-cell transplantation: ventricular arrhythmia frequency of animals after hiPSC-CM transplantation.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. DEFINITION

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms “a” and “an” include the plural reference unless the context clearly indicates otherwise. Also, as used herein and in the claims, the terms “at least one” and “one or more” have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term “about” generally means within 10%, 5%, 1%, or 0.5% of a given value or range. Alternatively, the term “about” means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term “about”. Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, the term “cardiomyocytes” is given its ordinary meaning in the art and refers to sarcomere-containing striated muscle cells, which are found in the mammalian heart, as opposed to skeletal muscle cells. The term “cardiomyocyte” as used herein includes any cardiomyocyte subpopulation or cardiomyocyte subtype, e.g. atrial, ventricular and pacemaker cardiomyocytes.

As used herein, the term “human induced pluripotent stem cell” (hiPSC) is a type of pluripotent stem cell artificially derived from a non-pluripotent cell, typically an adult somatic cell, via inducing the expression of certain de-differentiation genes in the non-pluripotent cell, e.g., Oct3/4, Sox2, Klf4 and/or c-Myc genes. Human induced pluripotent stem cells are identical to human embryonic stem cells in the ability to form any adult cell, but are not derived from an embryo.

The term “delete” or “deletion” when used in reference to a gene refers to the partial or complete removal of nucleic acid sequence as it normally presents, or the partial or complete inactivation of nucleic acid sequence as it normally functions. Specifically, in the present disclosure, a deletion in a sequence means the removal of all or part of the sequence which may results in the complete or partial inactivation of the sequence. Deletions, or disruptions will render the gene or coding sequence “non-functional” within the meaning the present disclosure. According to the present disclosure, the expression of “deletion in HCN gene” and its grammatical equivalents (e.g., deletion in HCN1, HCN2, HCN3 or HCN4 gene) refer to a cardiomyocyte wherein a nucleic acid encoding all amino acids or a subset of the amino acids of HCN (e.g., HCN1, HCN2, HCN3 or HCN4) are not present. According to the present invention, if the cardiomyocyte comprising a deletion in the HCN gene has a residual nucleic acid encoding a subset of the amino acids of HCN, said residual nucleic acid is incapable of producing a functional gene product or the gene product is incapable of generating current in the heart.

The terms “administered”, “administering” and “administration” are used interchangeably herein to refer a mode of delivery. According to some embodiments, the present cardiomyocytes are intramyocardially injected to a subject in need thereof (e.g., a subject having or suspected of having a cardiac disease). In some preferred embodiments, the present cardiomyocytes are administered to the left ventricle of the heart of the subject.

As used herein, the terms “treating” and “treatment” are interchangeable, and encompass partially or completely preventing, ameliorating, mitigating and/or managing a symptom, a secondary disorder or a condition associated with cardiac disease. The term “treating” as used herein refers to application or administration of the present cardiomyocytes to a subject, who has a symptom, a secondary disorder or a condition associated with cardiac disease, with the purpose to partially or completely alleviate, ameliorate, relieve, delay onset of, inhibit progression of, reduce severity of, and/or reduce incidence of one or more symptoms, secondary disorders or features associated with cardiac disease. Symptoms, secondary disorders, and/or conditions associated with cardiac disease include, but are not limited to, chest pain, chest tightness, chest pressure, chest discomfort (e.g., angina pectoris), shortness of breath, dizziness, lightheadedness, fainting (syncope), fluttering in the chest, slow heartbeat (bradycardia), racing heartbeat (tachycardia), and fatigue. Treatment may be administered to a subject who exhibits only early signs of such symptoms, disorder, and/or condition for the purpose of decreasing the risk of developing the symptoms, secondary disorders, and/or conditions associated with cardiac disease. Treatment is generally “effective” if one or more symptoms or clinical markers are reduced as that term is defined herein. Alternatively, a treatment is “effective” if the progression of a symptom, disorder or condition is reduced or halted.

The term “effective amount” as referred to herein designate the quantity of a component which is sufficient to yield a desired response. For therapeutic purposes, the effective amount is also one in which any toxic or detrimental effects of the component are outweighed by the therapeutically beneficial effects. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed. Effective amount may be expressed, for example, in cell numbers of body weight (cells/Kg), cell numbers of body surface area (cells/$m^2$), or cell numbers per subject (cells/subject). Persons having ordinary skills could calculate the human equivalent dose (HED) for the medicament (such as the present cardiomyocytes) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The term "subject" refers to a mammal including the human species that can be subjected to the isolated population of cardiomyocytes, pharmaceutical composition and/or method of the present invention. The term "subject" is intended to refer to both the male and female gender unless one gender is specifically indicated.

II. DESCRIPTION OF THE INVENTION

The present disclosure is based, at least in part, on the unexpected discovery that the deletion of HCN genes, especially HCN1 and HCN4 genes, in hiPSC-derived cardiomyocytes (i.e., the cardiomyocytes differentiated from hiPSCs, hereinafter as "hiPSC-CMs) reduces the risk or tissue electrical disturbance and arrhythmia after transplantation into a subject. Accordingly, the present disclosure is directed to a population of hiPSC-CMs, and uses thereof in treating cardiac diseases. According to some embodiments of the present disclosure, the administration of the present hiPSC-CMs is useful in treating cardiac diseases without causing adverse effect, e.g., ventricular arrhythmias, in a subject.

The first aspect of the present disclosure is thus directed to a population of hiPSC-CMs. According to the embodiments of the present disclosure, the present population of hiPSC-CMs is characterized by having deletions in HCN1 and HCN4 genes, and accordingly, does not express HCN isoforms 1 and 4, i.e., HCN1 and HCN4. According to some preferred embodiments of the present disclosure, in addition to the deletions in HCN1 and HCN4 genes, the present population of hiPSC-CMs further comprises deletions in HCN2 and HCN3 genes; in these embodiments, the population of hiPSC-CMs does not express HCN isoforms 1, 2, 3 and 4, i.e., HCN1, HCN2, HCN3 and HCN4.

According to some exemplary embodiments of the present disclosure, the population of hiPSC-CMs is produced from the hiPSCs by a method comprising, (a) making deletions in the HCN genes of the hiPSCs; and
(b) incubating the HCN-deleted hiPSCs of step (a) in a differentiation medium to induce differentiation of the HCN-deleted hiPSCs into the population of cardiomyocytes.

The hiPSCs for producing the present hiPSC-CMs may be obtained by any methods known in the art; for example, modifying the expression of transcription factors in human somatic cells so as to reprogram (di-differentiate) the somatic cells into pluripotent cells. Non-limiting examples of human somatic cells suitable to produce the present hiPSCs include, peripheral blood mononuclear cells (PBMCs), fibroblasts (e.g., epithelial fibroblasts from skin), keratinocytes (e.g., keratinocytes from hair follicles), mesenchymal stem cells (MSCs, e.g., mesenchymal stem cells from teeth or adipose tissue), epithelial cells (e.g., renal or gastric epithelial cells), hepatocytes, immune cells (e.g., T or B cells from peripheral blood), hematopoietic stem cells (HSCs), and bone marrow cells (BMCs). According to one exemplary embodiment, the hiPSC is derived from PBMCs.

Examples of transcription factors suitable for reprogramming somatic cells into pluripotent cells (e.g., the present hiPSCs) include, but are not limited to, octamer-binding transcription factor 3 (Oct3), Oct4, sex-determining region Y-box 1 (Sox1), Sox2, Sox3, Sox15, Sox18, Kruppel Like Factor (Klf1), Klf2, Klf4, Klf5, c-Myc, Nanog, LIN28, Glis1, and the combination thereof. According to some embodiments, human somatic cells are reprogramming into pluripotent cells by use of a four-factor reprogramming cocktail, known as "OSKM", which include transcription factors Oct4, Sox2, KLF4 and c-Myc. According to certain embodiments, human somatic cells are reprogrammed by a six-factor reprogramming cocktail that includes transcription factors Oct4, Sox2, Klf4, c-Myc, Nanog and Lin28. Alternatively, one or more factors of the reprogramming cocktail OSKM (e.g., Klf4) may be in combination with other factors known to regulate the reprogramming process, for example, p53 inhibitor (e.g., p53 shRNA or SV40LT), miR-302b, miR-372, tranylcypromine, valproic acid (VPA), CHIR99021 (a GSK-3 inhibitor), E-616452 (an Alk5 inhibitor), or a combination thereof. As could be appreciated, the transcription factors used to reprogram the somatic cells into hiPSCs vary with the cells source and/or reprogramming method. A skilled artisan may select suitable transcription factors for the reprogramming process in accordance with intended purpose. According to some exemplary embodiment, transcription factors Oct4, Sox2, Klf4 and c-Myc are used to reprogram the somatic cells (e.g., PBMC) into hiPSCs.

Depending on desired purpose, the somatic cells may be reprogrammed via a viral or non-viral method, i.e., modifying the expression of transcription factors in the somatic cells with the aid of a viral vector or by use of a non-viral method to induce the somatic cells into hiPSCs. Specifically, in the viral method, the nucleic acid(s) encoding the transcription factors is/are introduced into the somatic cells via a viral vector; exemplary viral vectors suitable for this purpose include, but are not limited to, sendai virus, adenovirus, adeno-associated virus (AAV), retrovirus, lentivirus, and sindbis virus. In the non-viral method, the nucleic acid(s) encoding the transcription factors is/are introduced into the somatic cells via a non-viral technique, such as mRNA transfection, miRNA transfection or infection, transposons (e.g., PiggyBac and Sleeping Beauty), plasmid transfection, liposomal magnetofection, minicircle transfection, or other methods known to introduce a nucleic acid into a host cell. Alternatively, the transcription factors may be in vitro synthesized by prokaryotic or eukaryotic systems, and then administered to the somatic cells for the reprogramming purpose. Still alternatively, the hiPSCs may be produced by chemical induction, i.e., treating the somatic cells with chemicals (e.g., cAMP agonists and/or epigenetic modulators) to induce the reprogramming process.

In the step (a), the hiPSCs obtained by any method described above are genetically modified to comprise deletions in HCN genes. The HCN genes (i.e., HCN1, HCN2, HCN3 and/or HCN4 genes) may be deleted from the genome of the hiPSC by any gene-knockout technique known in the art, in which a specific gene is partially or completely removed from the genomic DNA of a cell or a model organism to prevent said specific gene from expression. Examples of gene-knockout technique include, but are not limited to, Cre and Lox recombination, clustered regularly interspaced short palindromic repeats (CRISPR) genome editing, homologous recombination, site-specific nucleases, zinc-fingers, and transcription activator-like effector nucleases (TALENs). According to one exemplary embodiment, the HCN genes are deleted from the genome of the hiPSC by CRISPR genome editing. The CRISPR mechanism and the procedures for carrying out the CRISPR technique are known by the person having ordinary skill in the art; hence, the detailed description is omitted herein, for the sake of brevity.

According to some embodiments of the present disclosure, the HCN1 and HCN4 genes are absent in the modified hiPSCs (i.e., $HCN1^-/HCN4^-$ hiPSCs). According to some preferred embodiments of the present disclosure, the HCN1, HCN2, HCN3, and HCN4 genes are absent in the modified hiPSCs (i.e., $HCN1^-/HCN2^-/HCN3^-/HCN4^-$ hiPSCs).

In the step (b), the HCN-deleted hiPSCs of step (a) are incubated in a differentiation medium. Depending on desired purpose, the differentiation medium may comprise suitable differentiation factors and/or molecules associated with cardiomyocyte differentiation, for example, ascorbic acid (AA), activin A, basic fibroblast growth factor (bFGF), bone morphogenetic protein 2 (BMP2), BMP4, dickkopf-1 (DKK1), an inhibitor of glycogen synthase kinase-3 (GSK-3) (e.g., CHIR99021), noggin (Ngn), stem cell factor (SCF), vascular endothelial growth factor (VEGF), an inhibitor of WNT pathway (such as IWP-1, IWP-2, IWP-4 or IWR-1), or a combination thereof, so that the HCN-knockout hiPSCs would differentiate into HCN-knockout hiPSC-CMs. According to some exemplary embodiments, the hiPSCs are incubated in a differentiation medium containing B-27™ serum free supplement, bFGF, ascorbic acid, GSK-3 inhibitor and WNT inhibitor. As could be appreciated, a skilled artisan may select suitable differentiation medium for the differentiation process in accordance with practical applications.

According to some embodiments, the cardiomyocytes derived from the $HCN1^-/HCN4^-$ hiPSCs (i.e., $HCN1^-/HCN4^-$ hiPSC-CMs) comprise a deletion of exon 3 of HCN1 gene, and a deletion of exon 6 of HCN4 gene. According to certain preferred embodiments, the $HCN1^-/HCN4^-$ hiPSC-CMs comprise a deletion from nucleotide positions 1235 to 1254 in the HCN1 gene (SEQ ID NO: 1, or NCBI Reference Sequence: NM_021072.4), and a deletion from nucleotide positions 2509 to 2528 in the HCN4 gene (SEQ ID NO: 4, or NCBI Reference Sequence: XM_033189457.1). In these embodiments, the population of $HCN1^-/HCN4^-$ hiPSC-derived CMs does not express HCN1 and HCN4.

According to some embodiments, the cardiomyocytes derived from the $HCN1^-/HCN2^-/HCN3^-/HCN4^-$ hiPSCs (i.e., $HCN1^-/HCN2^-/HCN3^-/HCN4^-$ hiPSC-CMs) comprise a deletion of exon 3 of HCN1 gene, a deletion of exon 2 of HCN2 gene, a deletion of exon 3 of HCN3 gene, and a deletion of exon 6 of HCN4 gene. According to certain preferred embodiments, the $HCN1^-/HCN2^-/HCN3^-/HCN4^-$ hiPSC-CMs comprise a deletion from nucleotide positions 1235 to 1254 in the HCN1 gene (SEQ ID NO: 1, or NCBI Reference Sequence: NM_021072.4), a deletion from nucleotide positions 883 to 902 in the HCN2 gene (SEQ ID NO: 2, or NCBI Reference Sequence: XM_018560576.1), a deletion from nucleotide positions 796 to 815 in the HCN3 gene (SEQ ID NO: 3, or NCBI Reference Sequence: XM_004315601.3), and a deletion from nucleotide positions 2509 to 2528 in the HCN4 gene (SEQ ID NO: 4, or NCBI Reference Sequence: XM_033189457.1). In these embodiments, the population of $HCN1^-/HCN2^-/HCN3^-/HCN4^-$ hiPSC-CMs does not express HCN1, HCN2, HCN3 and HCN4.

The HCN-deleted hiPSC-CMs of step (b) are then isolated from the differentiation medium by gravity or centrifugation (e.g., centrifuge at the speed of 100×g at room temperature or 4 °C for 1-10 minutes), thereby producing the isolated population of HCN-deleted hiPSC-CMs.

As could be appreciated, the present cardiomyocytes may alternatively be derived from human embryonic stem cells (hESCs). The method of producing cardiomyocytes from hESCs is quite similar to the method of producing cardiomyocytes from hiPSCs described above. Therefore, the detailed description is omitted herein, for the sake of brevity.

The second aspect of the present disclosure pertains to a pharmaceutical composition for treating cardiac disease in a subject in need of such treatment. According to certain embodiments of the present disclosure, the pharmaceutical composition comprises the HCN-deleted hiPSC-CMs produced in accordance with any embodiments of the present disclosure, and a pharmaceutically acceptable carrier.

According to various embodiments of the present disclosure, the pharmaceutical composition may be formulated into a dosage form suitable for administration through a desired route. As could be appreciated, the HCN-deleted hiPSC-CMs can be administered into any area of the heart where conduction disturbances have occurred. According to some preferred embodiments, the HCN-deleted hiPSC-CMs are administered to the left ventricle of the heart. The number of the HCN-deleted hiPSC-CMs necessary to be therapeutically effective varies with the type of disorder being treated as well as the extent of the overall damage of myocardial tissue, among other factors. A particularly suitable administration mode can be in situ application of the present HCN-deleted hiPSC-CMs or pharmaceutical composition to a cardiac tissue by, for example, direct surgical application. Another particularly suitable administration mode can be catheter injection of the present HCN-deleted hiPSC-CMs or pharmaceutical composition to a cardiac tissue. There are many known techniques that can be used to facilitate the access to the administration site. For example, the catheter injection may be used in connection with a fluoroscopy, X-ray, echocardiography, or magnetic resonance imaging guiding system. It should be noted that the above-mentioned administration routes are provided for the purpose of discussion, and the present disclosure is not limited to these administration modes. Rather, according to some embodiments, the HCN-deleted hiPSC-CMs or pharmaceutical compositions may be administered systemically. Illustrative examples of dosage forms of the pharmaceutical composition include suspensions, dispersions, solutions, ointments, pastes, powders, dressings, creams, and gels. As could be appreciated, these pharmaceutical compositions are also within the scope of the present disclosure.

Preferably, the present pharmaceutical composition is formulated into liquid forms, e.g., sterile suspensions that can be administered by intramyocardial injection. More preferably, the volume of the present pharmaceutical composition is less than 10 milliliter (mL), for example, less than 9, 8, 7, 6, 5, 4, 3, 2, 1, 0.9, 0.8, 0.7, 0.6, 0.5, 0.4, 0.3, 0.2 or 0.1 mL.

The third aspect of the present disclosure provides a method for treating a cardiac disease in a subject. The method comprises administered to the subject effective amount of the present hiPSC-CMs (i.e., HCN-deleted hiPSC-CMs) or pharmaceutical composition so as to ameliorate or alleviate the symptoms of the cardiac disease.

According to certain exemplary embodiments of the present disclosure, the effective amount of the present hiPSC-CMs for treating the cardiac disease is about $1\times10^5$ to $1\times10^9$ cells per transplant dose, such as $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times 10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, or $1\times10^9$ cells per transplant dose. In some exemplary embodiments, the pharmaceutical composition comprises $1\times10^5$ to $1\times10^9$ hiPSC-CMs so as to achieve the therapeutic purpose.

Preferably, the present hiPSC-CMs or pharmaceutical composition is intramyocardially administered to the subject. More preferably, the present hiPSC-CMs or pharmaceutical composition is administered to the left ventricle of the heart of the subject.

According to some examples of the present disclosure, the administered hiPSC-CMs are viable and functional in the subject for at least 6 months, for example, 6, 7, 8, 9, 10, 11 or 12 months, or longer.

Depending on desired purpose, the present hiPSCs and the hiPSC-CMs derived therefrom may be derived from the subject being treated/administered (i.e., autologous transplantation), another subject of the same species (i.e., allogeneic transplantation), or a subject of different species (i.e., xenogeneic transplantation). Preferably, said transplantation is autologous transplantation or allogeneic transplantation. In the case when the transplantation is allogeneic transplantation, the present hiPSCs or hiPSC-CMs are further modified to inhibit the expression of major histocompatibility complex (MHC), for example, making a deletion or mutation in MHC genes. Alternatively, the method further comprises the step of administering to the subject an immunosuppressive treatment prior to, concurrently with, or after the administration of present hiPSC-CMs, so as to suppress the immune response of the subject against the allogeneic hiPSC-CMs. The immunosuppression may be achieved by any agent and/or method known by a skilled artisan to prevent graft rejection, for example, the administration of gamma irradiation or immunosuppressant.

Depending on desired purposes, the immunosuppressant may be a glucocorticoid (e.g., prednisone, budesonide, prednisolone, dexamethasone or hydrocortisone), janus kinase inhibitor (e.g., tofacitinib), calcineurin inhibitor (e.g., cyclosporine or tacrolimus), mTOR inhibitor (e.g., sirolimus or everolimus), inhibitor of inosine monophosphate dehydrogenase (IMDH inhibitor; e.g., azathioprine, leflunomide or mycophenolate), biologics or monoclonal antibody (e.g., abatacept, adalimumab, anakinra, certolizumab, etanercept, golimumab, infliximab, ixekizumab, natalizumab, rituximab, secukinumab, tocilizumab, ustekinumab, vedolizumab, basiliximab or daclizumab), or any agent known to suppress or reduce the immune response, such as methotrexate or mercaptopurine. A clinical practitioner or a skilled artisan may determine the type of immunosuppressant and treatment regimen in accordance with the physical conditions of the subject.

According to some embodiments, the administration of the present hiPSC-CMs or pharmaceutical composition is useful in treating the cardiac disease, without causing ventricular arrhythmia in the subject. According to certain embodiments, the administration of the present hiPSC-CMs or pharmaceutical composition alleviates post-transplant ventricular arrhythmia.

Non-limiting examples of the cardiac disease treatable with the present hiPSC-CMs, pharmaceutical composition and/or method include, myocardial infarction, cardiac arrhythmia, myocardial ischemia, cardiac failure, angina pectoris, or a combination thereof. According to one exemplary embodiment, the cardiac disease is myocardial infarction.

The subject treatable by the present method is a mammal, for example, a human, mouse, rat, guinea pig, hamster, monkey, swine, dog, cat, horse, sheep, goat, cow, and rabbit. Preferably, the subject is a human.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

Example

Materials and Methods

Preparation of hiPSCs

In the present disclosure, the hiPSCs were prepared from human peripheral blood mononuclear cells (PBMCs) via the following steps:

(1) culturing the PBMCs in RPMI 1640 medium supplemented with 10% fetal bovine serum (FBS) and 1% penicillin/streptomycin at a 5% $CO_2$ incubator at 37 °C;

(2) genetically modifying the PBMCs (transduction of reprogramming factors) with sendai virus vectors to express transcription factors Oct4, Sox2, Klf4, and c-Myc;

(3) culturing the PBMCs of step (2) in STEMFLEX™ medium to support their survival and proliferation; and (4) isolating the generated hiPSC colonies, followed by expanding the hiPSCs to establish stable cell lines; the pluripotent nature of the thus-obtained hiPSCs were determined by assessing their morphology, surface marker expression, and ability to differentiate into cells representative of the three germ layers.

Preparation of HCN-Deleted hiPSCs

For the purpose of producing $HCN1^-/HCN4^-$ hiPSCs, CRISPR technology was used to delete HCN1 and HCN4 genes from the genome of hiPSCs. To target the coding sequences of the human HCN genes, the following CRISPR sequences were annealed and ligated into the All-In-One (AIO) vectors containing the Cas9 expression cassette, including the CRISPR guide RNAs, 5'-GTTCTTAGTACCACTACTGC-3' (SEQ ID NO: 5) for HCN1 gene and 5'-GTGCGCATCGTGAACCTCAT-3' (SEQ ID NO: 6) for HCN4 gene. The CRISPR transfection was performed in the order of HCN1 and HCN4. The transfected hiPSCs were cultured with STEMFLEX™ medium and then dissociated into single cells using 0.05% trypsin. The single cells were seeded in wells of a 96-well cell culture dish and expanded into colonies. Finally, real-time PCR was used to detect CRISPR editing efficiency.

The thus-produced the HCN1⁻/HCN4⁻ hiPSCs had a deletion from nucleotide positions 1235 to 1254 in the HCN1 gene (SEQ ID NO: 1) and a deletion from nucleotide positions 2509 to 2528 in the HCN4 gene (SEQ ID NO: 4).

For the purpose of producing HCN1⁻/HCN2⁻/HCN3⁻/HCN4⁻ hiPSCs, CRISPR technology was used to delete HCN1, HCN2, HCN3 and HCN4 genes from the genome of hiPSCs. To target the coding sequence of the human HCN genes, the following CRISPR sequences were annealed and ligated into the All-In-One (AIO) vectors containing the Cas9 expression cassette, including the CRISPR guide RNAs, 5'-GTTCTTAGTACCACTACTGC-3' (SEQ ID NO: 5) for HCN1 gene, 5'-AGTACAGTTCACTCCACGAG-3' (SEQ ID NO: 7) for HCN2 gene, 5'-ATGTCACTGGGATGGCTGTC-3' (SEQ ID NO: 8) for HCN3 gene, and 5'-GTGCGCATCGTGAACCTCAT-3' (SEQ ID NO: 6) for HCN4 gene. The CRISPR transfection was performed in the order of HCN1, HCN4, HCN2, and HCN3. The transfected hiPSCs were cultured with STEMFLEX™ medium and then dissociated into single cells using 0.05% trypsin. The single cells were seeded in wells of a 96-well cell culture dish and expanded into colonies. Finally, real-time PCR was used to detect CRISPR editing efficiency.

The thus-produced the HCN1⁻/HCN2⁻/HCN3⁻/HCN4⁻ hiPSCs had a deletion from nucleotide positions 1235 to 1254 in the HCN1 gene (SEQ ID NO: 1), a deletion from nucleotide positions 883 to 902 in the HCN2 gene (SEQ ID NO: 2), a deletion from nucleotide positions 796 to 815 in the HCN3 gene (SEQ ID NO: 3), and a deletion from nucleotide positions 2509 to 2528 in the HCN4 gene (SEQ ID NO: 4).

Preparation of HCN-Deleted hiPSC-CMs from HCN-Deleted hiPSCs

The HCN-deleted hiPSCs were cultured in MEM a (a modification of Minimum Essential Medium (MEM) containing non-essential amino acids, sodium pyruvate, lipoic acid, vitamin $B_{12}$, biotin, and ascorbic acid), supplemented with 4 ng/mL bFGF. On day −1, $1.4\times10^6$ cells were seeded into a 6-well plate coated with MATRIGEL®. The culture medium was replaced with RPMI medium containing GSK-3 inhibitor (5 M CHIR99021) and B-27™ supplement minus insulin (a complete B-27™ supplement without insulin that contained biotin, DL-alpha tocopherol acetate, DL-alpha tocopherol, vitamin A, bovine serum albumin, catalase, human transferrin, superoxide dismutase, corticosterone, D-galactose, ethanolamine HCl, glutathione, L-carnitine HCl, linoleic acid, linolenic acid, progesterone, putrescine, sodium selenite and triodo-I-thyronine) on day 0. The cells were incubated at 37 °C for two days. The medium was replaced with RPMI medium containing B-27™ supplement minus insulin on day 2, followed by incubating the cells at 37 °C for 24 hours.

On day 3, the medium was changed to RPMI medium containing WNT inhibitor (5 μM IWR-1) and B-27™ supplement minus insulin. Two days later (day 5), the WNT inhibitor was removed from the culture medium (i.e., culturing the cells with RPMI medium containing B-27™ supplement minus insulin). The medium was further changed to RPMI medium containing complete B-27™ supplement (with insulin) on day 7. The medium was replaced with fresh medium every two days. On day 12, the culture medium was removed, and RPMI (no glucose) containing B-27™ supplement (with insulin) was added to the well. The medium was replaced with fresh medium every two days. On day 16, the medium was replaced with RPMI containing B-27™ supplement (with insulin) so as to obtain the HCN-deleted hiPSC-CMs.

According to the analytic results, the HCN1⁻/HCN4⁻ hiPSC-CMs did not express HCN isoforms HCN1 and HCN2, and the HCN1⁻/HCN2⁻/HCN3⁻/HCN4⁻ hiPSC-CMs did not express HCN isoforms HCN1, HCN2, HCn3 and HCN4 (data not shown).

Animal Study

A myocardial infarction (MI) pig model (Lanyu Pig, 8 month-old, 35-45 kg) was established in the present study. One week prior to ischemia-reperfusion (I-R) surgery, an insertable cardiac monitor was implanted to the heart thereby recording the heart rhythm. Transthoracic echocardiogram (TTE) and pressure-volume (P-V) loop conductance catheterization were carried out to determine left ventricular (LV) function.

HCN1-4-deleted hiPSC-CMs ($1.5\times10^9$ cells/pig) and HCN-positive hiPSC-CMs ($1.5\times10^9$ cells/pig; serving as control group) were respectively administered to the left ventricles of the animals' hearts two weeks post I-R surgery. After four weeks, the LV function of the animals receiving HCN-deleted hiPSC-CMs (n=8) or HCN-positive hiPSC-CMs (n=6) was determined by TTE and P-V loop analysis, and the electrocardiogram (ECG) of the animals was recorded.

Statistical Analysis

All statistical analyses were performed using software. The results were analyzed using the unpaired Student's t-test or one-way ANOVA test to compare two independent groups or more than two comparisons, respectively. For each result, all data are presented as the means±S.D. from three independent experiments. * $P<0.05$,  $P<0.01$, * $P<0.001$, and ns indicates no significance for 95% two-tail confidence intervals.

Example 1 Characterization of hiPSC-CMs

The biophysical characteristics of membrane ion currents in hiPSC-CMs were investigated in the example. First, the whole-cell configuration of the patch-clamp technique was conducted to examine the kinetic properties of sodium current ($I_{Na}$) in hiPSC-CMs. It is known that the magnitude of $I_h$ is closely linked to the extent of pacemaker potential in different types of electrically excitable cells. Thus, RNA sequencing and quantitative polymerase chain reaction (qPCR) were used to identify whether hPSC-CMs had HCN expression. The data indicated that the expression of HCN1 and HCN4 was much higher in hiPSC-CMs than that in hiPSCs (data not shown).

These data suggested that compared to hiPSCs, the cardiomyocytes derived from hiPSCs (i.e., hiPSC-CMs) exhibited higher expression level of HCN proteins, especially HCN1 and HCN4.

Example 2 In Vivo Study

The slope of end-systolic elastane (Ees) represents the end-systolic pressure-volume P-V relationship (ESPVR), and serves as an index of myocardial contractility. According to the TTE and P-V loop analysis, compared to the control group (i.e., the animals without I-R surgery), the VL function decreased in the animals receiving I-R surgery, in which the left ventricular ejection fraction (LVEF) declined from 74.0±3.3% to 38.5±4.4% (n=5, p<0.001) and the Ees was reduced from 6.24±1.17 to 2.41±0.74 (n=5, p<0.001) (data not shown).

The data of insertable cardiac monitor indicated that there was no ventricular arrhythmia episode before I-R surgery. However, ventricular tachycardia (VT) episodes, which could be spontaneously converted to sinus rhythm, were detected during I-R surgery (data not shown). The cycle length of these VT episodes during I-R surgery was measured. According to the results, the QRS width of VT in Lanyu pigs was ≥60 msec, while the infarcted Lanyu pigs exhibited non-sustained and sustained VT episodes of 11±9 and 59±22, respectively (data not shown). The longest duration and the fastest heart beats were 55 minutes and 375 beats per minute (BPM) (data not shown). These pigs still could survive with good activity during VT attacks.

The established MI pig model was used to evaluate the effect of the present HCN-deleted hiPSC-CMs on treating MI. The data of FIG. 1 demonstrated that intramyocardial injection of HCN-deleted hiPSC-CMs alleviated post-transplant ventricular arrhythmia as compared to the control group (HCN-positive hiPSC-CMs), suggesting that intramyocardial delivery of HCN-deleted hiPSC-CMs would not increase the risk of ventricular arrhythmogenicity after intramyocardial transplantation.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. An isolated population of cardiomyocytes differentiated from human induced pluripotent stem cells (hiPSCs), comprising genomic deletions in HCN1, HCN2, HCN3 and HCN4 genes, wherein the deletion in the HCN1 gene is a deletion of nucleotides 1235-1254 of the sequence set forth by SEQ ID NO: 1;

the deletion in the HCN2 gene is a deletion of nucleotides 883-902 of the sequence set forth by SEQ ID NO: 2;

the deletion in the HCN3 gene is a deletion of nucleotides 796-815 of the sequence set forth by SEQ ID NO: 3; and the deletion in the HCN4 gene is a deletion of nucleotides 2509-2528 of the sequence set forth by SEQ ID NO: 4.

2. The isolated population of cardiomyocytes of claim 1, wherein the isolated population of cardiomyocytes is produced by a method comprising, (a) making deletions in the HCN1, HCN2, HCN3 and HCN4 genes of the hiPSCs; and (b) incubating the hiPSCs of step (a) in a differentiation medium to induce differentiation of the hiPSCs into the population of cardiomyocytes.

* * * * *

SEQUENCE LISTING

```
Sequence total quantity: 8
SEQ ID NO: 1            moltype = DNA  length = 9933
FEATURE                 Location/Qualifiers
source                  1..9933
                        mol_type = genomic DNA
                        organism = Homo sapiens
SEQUENCE: 1
gagccgagct gagcctcgcc tagctccggc agcctcagct tcagcaccag ccgcaccgga  60
gcccggaccg cagccactaa gggcagcggc ggcggcggga gccaggcgcg cagctagcag  120
cggcgcggtc gggaagcagc agccgccgcc gccgccgccg ccgccgcgac gggcagctgg  180
gctcgccggc agccggctcg ggcccctacc ctctcggcta cgtgtctccg gcgccgggcg  240
gccggcgagt ctggagcccg cgccgtcgcc ggccgcgtcc tccgggcatg gaaggaggcg  300
gcaagcccaa ctcttcgtct aacagccggg acgatggcaa cagcgtcttc cccgccaagg  360
cgtccgcgac gggcgcgggg ccggccgcgg ccgagaagcg cctgggcacc ccgccggggg  420
gcggcggggc cggcgcgaag gagcacggca actccgtgtg cttcaaggtg gacggcggtg  480
gcggcggtgg cggcggcggc ggcggcggcg aggagccggc gggggcttc gaagacgccg  540
aggggccccg gcggcagtac ggcttcatgc agaggcagtt cacctccatg ctgcagcccg  600
gggtcaacaa attctccctc cgcatgtttg ggagccagaa ggcggtggaa aaggagcagg  660
aaagggttaa aactgcaggc ttctggatta tccaccctta cagtgatttc aggttttact  720
gggatttaat aatgcttata atgatggttg gaaatctagt catcatacca gttggaatca  780
cattctttac agagcaaaca acaacaccat ggattatttt caatgtggca tcagatacag  840
ttttcctatt ggacctgatc atgaatttta ggactgggac tgtcaatgaa gacagttctg  900
aaatcatcct ggaccccaaa gtgatcaaga tgaattattt aaaaagctgg tttgtggttg  960
acttcatctc atccatccca gtggattata tctttcttat tgtagaaaaa ggaatggatt  1020
ctgaagttta caagacagcc agggcacttc gcattgtgag gtttacaaaa attctcagtc  1080
tcttgcgttt attacgactt tcaaggttaa ttagatacat acatcaatgg gaagagatat  1140
tccacatgac atatgatctc gccagtgcag tggtgagaat ttttaatctc atcggcatga  1200
tgctgctcct gtgccactgg gatggttgtc ttcagttctt agtaccacta ctgcaggact  1260
tcccaccaga ttgctgggtg tctttaaatg aaatggttaa tgattcttgg ggaaagcagt  1320
attcatacgc actcttcaaa gctatgagtc acatgctgtg cattgggtat ggagcccaag  1380
ccccagtcag catgtctgac ctctggatta ccatgctgag catgatcgtc ggggccacct  1440
gctatgccat gtttgtcggc catgccaccg ctttaatcca gtctctggat tcttcgaggc  1500
ggcagtatca agagaagtat aagcaagtgg aacaatacat gtcattccat aagttaccag  1560
ctgatatgcg tcagaagata catgattact atgaacacag ataccaaggc aaaatctttg  1620
atgaggaaaa tattctcaat gaactcaatg atcctctgag agaggagata gtcaacttca  1680
actgtcggaa actggtggct acaatgcctt tatttgctaa tgcggatcct aattttgtga  1740
ctgccatgct gagcaagttg agatttgagg tgtttcaacc tggagattat atcatacgag  1800
aaggagccgt gggtaaaaaa atgtatttca ttcaacacgg tgttgctggt gtcattacaa  1860
aatccagtaa agaaatgaag ctgacagatg gctcttactt tggagagatt tgcctgctga  1920
ccaaaggacg tcgtactgcc agtgttcgag ctgatacata ttgtcgtctt tactcacttt  1980
ccgtggacaa tttcaacgag gtcctggagg aatatccaat gatgaggaga gcctttgaga  2040
cagttgccat tgaccgacta gatcgaatag gaaagaaaaa ttcaattctt ctgcaaaagt  2100
tccagaagga tctgaacact ggtgttttca acaatcagga gaacgaaatc ctcaagcaga  2160
ttgtgaaaca tgacagggag atggtgcagg caatcgctcc catcaattat cctcaaatga  2220
caaccctgaa ttccacatcg tctactacga ccccgacctc ccgcatgagg acacaatctc  2280
caccggtgta cacagcgacc agcctgtctc acagcaacct gcactccccc agtcccagca  2340
cacagacccc ccagccatca gccatcctgt caccctgctc ctacaccacc gcggtctgca  2400
gccctcctgt acagagccct ctggccgctc gaactttcca ctatgcctcc cccaccgcct  2460
cccagctgtc actcatgcaa cagcagccgc agcagcaggt acagcagtcc cagccgccgc  2520
agactcagcc acagcagccg tccccgcagc cacagacacc tggcagctcc acgccgaaaa  2580
atgaagtgca caagagcacg caggcgcttc acaacaccaa cctgacccgg gaagtcaggc  2640
cactctccgc ctcgcagccc tcgctgcccc atgaggtgtc cactctgatt tccagacctc  2700
atcccactgt gggcgagtcc ctggcctcca tccctcaacc cgtgacggcg gtccccggaa  2760
cgggccttca ggcagggggc aggagcactg tcccgcagcg cgtcaccctc ttccgacaga  2820
```

-continued

```
tgtcgtcggg agccatcccc ccgaaccgag gagtccctcc agcacccccct ccaccagcag  2880
ctgctcttcc aagagaatct tcctcagtct taaacacaga cccagacgca gaaaagccac  2940
gatttgcttc aaatttatga tccctgctga ttgtcaaagc agaaagaaat actctcataa  3000
actgagacta tactcagatc ttattttatt ctatctcctg atagatccct ctagcctact  3060
atgaagagat attttagaca gctgtggcct acacgtgaaa tgtaaaaata tatatacata  3120
tactataaaa tatatatcta aattcccaag agagggtcaa aagacctgtt tagcattcag  3180
tgttatatgt cttcctttct ttaaatcatt aaaggattta aaatgtcgtt gtaagattat  3240
ttatttctaa cctactttta cttaagtcct ttgatatgta tatttctcta ttttatgaag  3300
agttcttgga ttcaatggaa acaaaactga ttttaaaaag gcaactcaaa tgaactagta  3360
aatagcacca atcaaaactt tctttcatta gctgtgtctc tgcatctaaa ttgttaatca  3420
ttaatggtgg agaattaaat aacaaatccc attttataga tctaaattgt atttcggtgc  3480
tttcaatttc aaattaggtt aaagaatgca ctacttgctt ggccaccgta ggagactagc  3540
attgccactg tttgttaaga atatcactaa cctcaaacat gttcattgat ctttcagaaa  3600
gctgagggaa aattaatatt tgtcttcatg tgttatcgga cttttaccaa gactcgatca  3660
atgttagttg taaataactt tttcaaccca aataaaaata gctattctgt gttgtatgaa  3720
ggtaaaagtc attgtttaag aatttagttt tattgcttca cttcaaaact tagagtttta  3780
aattttacaa aacctgattg tgagaattat tcaattgtaa tgcaatggct tgaaacctac  3840
aatattattt taacctgcaa tgttttatgc aaaattgtat gctcgaatct acaaattgct  3900
tgtattacac caaaaatcgt tacttttctt tcttcttgcc ataatcaagc atctgaaaat  3960
agtccctgca tgcttctggg gaaaaaaaaa taggttcaaa tcagtcattg tagagaaagg  4020
cttacagtat ttctcgtttc tagaaaagca taacaattca ttaattgcct atcttataat  4080
tcctataagg ctgacttgga tctctgactt aagtctagaa gtgaggtttt cacttttatt  4140
taatattatt gctattatta tttaaataat tatttgtaaa ccacagcttg atttggagtt  4200
aagtgttgtc tgtgtcttca ctgtagctgg taatttacta tggtattaat ttaaagaaat  4260
aaattcaata cagcatcacg tctgtttggg aacacacatt ttgctctatg tatattgtaa  4320
ctaaatggtt agtaaacttt aaggcatgtg gtgactaacg tagcccttag ataggaggtt  4380
tgtcattttt aatgtgttga aaatagtaca gacatggtga cagaaagcag gggtaaagtt  4440
gaacgtctat gagcattgtc tgtctgtttt cttaactctt tacatgatct gtgagcacct  4500
gcttcttctc aaagaactcc cttagtaatc atttgtgcct aatgcatccc acacatgtgg  4560
agtatgactg gaacacaatt gaaagattcc taacaactgg ctgcggtaaa taacccaagt  4620
taagagcatg acttaaagtg gaggtcttca gtatctctgg cactggcaat acatttaaga  4680
acatacagag atcacacatt atgtgggaca gggcctgcag atagacttga ggacagaaaa  4740
caaaaacaaa agcagaaact ctaaagtgga tccttgctgc ctgttatgcc ttttgtggat  4800
ataataccta taataccaaa atgagttgtt atgtttaatt tcaaacaaat cccaactggt  4860
gtggaagtaa ttaactgcta gtcgatgtaa tgtaatcatc aatatgctgg tgacatatga  4920
tggcatgtca ggaatactgt tgtaagaaag ggattgttca gtctacctag aacctatggg  4980
aaagctgcaa gaccatttac atatcagtac aaaactcctt tattttatta aaatatgaga  5040
attaacttca atttattaag attacgtatt ggtcctttaa attattaaag gtttacattt  5100
gataggatta atggatttgg tagtgaaata tttttatata tataaatttt tggtttttta  5160
ttttgagcac tattgggaaa cataagcaaa attgaaatgc atggtctttc agtgcaacca  5220
tacaattttt attcactttg taatagaatg gacaaaaaaa ctaaggttta tatattaaac  5280
taataaaaag gtacagggta aattatatac atatatgtat gaatgtatat atacttagat  5340
taagaaaaaa aaatgactca cattcctgta atataaaggt ccattgctag ttgaaaagtg  5400
acctcttttc tctgtacata gtgaagcccg tatgtatgga gttttaatct gtacagaaag  5460
aaatgtatta ttcattggtc tttctgctgc tggaaagata atagaatagc tgattcttac  5520
aacaactgta tgatcaggga tgagttagag tatttctttt gtctttgctc aaagccatac  5580
atatataaat atatataaag attattaata aattcaacaa aaaataaact acaatcatga  5640
atattttatt ttatcaatat atgctaatca aatgttttat tttattaatg agtacagctt  5700
tgcctctatt tttacatcat aaaatttcca agagcttata cttgataatc acataaaatc  5760
aattatattc tataattctg gaatgagagg actttaaata gaacatggat ttttcaacca  5820
cttctttgtt taccttttc gtatagtaaa atatgagctt attttctttt ttgctctgtg  5880
ccttttttaga atgtggttgt tctccaactt caaaacacaa ccattttgtg taattattgg  5940
atatacagat gagaaataat tttcctgtaa taatggtaaa taattgtcct gtaatatatt  6000
tatacaaacc tattttgtta taatagttct atgacatacc tattttgtta taatagtttt  6060
ataacatacc tattttgtta taatagggcc ttgggctcta ttataacaaa acaggtttat  6120
ataaatacat tcatatttat agccttaaac aaaataggtt tgtatagtag gcccaaggcc  6180
ctattataac aaaataggtt tgtataaata tattcatatt tatagccttg ggccctgcaa  6240
agttatttgg agagtgatag aacctcccca cacaagtggg ttttaaatga tacctaaaag  6300
cctgagatag agtttatcat aatgagaata agtagtgaag cattcctgaa aacaaggagg  6360
ataaatagta gcaatggcaa tatattctat tcaccaaaaa agtagcttgt ctccaggtct  6420
ggatgacctc ttcataagtg aacaattccc tgatgaatgc tgttccactt taaagagatg  6480
gttattttgc aatttataaa cttaactgag catactattt tcaggacact acaaagtaca  6540
tagtcaagtt attaccgtca ttcctatagg acagagaatg atttaaacaa tatgacatgt  6600
ttaaaatttt agatgattta tttcaaatcc tgaattatgt ctacttcaaa ttatgagcaa  6660
tctctattat ctttcaggac tatttaaaaa atctccatac ctcctctttc agcttaggtt  6720
tttatatttg ttaattttac tatgttactt tgcttctatg gccctcactt gcactgttta  6780
taatgttaac ctgtttgaat gagatatctc tccattatat ctttatcttt ttagaacatg  6840
tgccataaaa cccatgtggt tattttgttc atatgcacta caactagcaa acttttattt  6900
tatgttcacc tactttaaaa agtactcata ctgtaccatg ggaaagaaac atgggcctta  6960
tagaatggaa tgctgagcta ttttgagtcc tgaaaacaat ggccaaaaat ttaaggaact  7020
gtggttgctg catgcaccaa attgtagcac atacaaataa ataaaataca gttctataac  7080
tgtattcaat atggttattt tcaaggaaaa ataggataga aattttcttt gaaagatttg  7140
ctattgtact tagggaagta cacctgctat taccctcaa aagcaatgac tttcttaagc  7200
aatttcaatt tttttccttt ttaacaaccc tgcacttgca caaccctgca tctcttgtct  7260
caccctaatg ctgaccctgc ttccaattca ggctttgaca gggacaaatg gagattttaa  7320
ggttttttaa tgagagaagc cttgctgaca ctcccgcat cccaccttga aaattattta  7380
aagatgatct taaaagaacc tacagataat gctctgaatt tgtttacaag gtccttgatg  7440
tggagagaat gagtaataca ttaaatgctg gggaaataat tatcatttag tgaaaaatta  7500
agcatgcttt tctaaaatgt ggatgtttaa cagagcacag ctgattggga acactggcag  7560
```

```
ttcaatgcag ctggagtgtc tcacagggtg aagaggaacc cagatcaagt gggaaatagg  7620
gatttcaaaa accttctgaa aggcttttaa catcagggca aaggttttac agtgttgtac  7680
tttatattct taatttaagc ttatcaacgg ggaggattca cattgaaatg tctgttttgc  7740
taatgtaaca aggaataaaa taatttatga cacagcaaaa actgggggct atttacaacc  7800
ccaccctgcc ttgtgaggat gctgggtcct aaggaaggtc ctaggtttgc taaatagagt  7860
aatgggaata ggaaactgaa agtttacttg ctttgcgtaa gataatatat tgcggcaggg  7920
aaggggtaca agaagataag agctagaacc tgtgagaagg gaaagaagtg ataaaataat  7980
tttggctaaa ataaagcaag ttctcaggcc aggcgtggtg gctcatgcct gtaatcctag  8040
cactttggga ggccaaagtg ggaggaatgc ttgaggccag gaattggaga ccaaccaggg  8100
cagcatgtca agacctggtc tctacaagga aaaaaaattt ttttaattga ccagtatata  8160
cttacatacc tgcagtgttt agaaaacccg actataggtg gtgtattcct gtagtcctag  8220
ttactcagaa agttaaggca ggaggatcgc ttgaacttag gaggtcaagg ctgcagtgag  8280
ccctgttcgt tccactgcac tccagcttgg gggacagagc aaaacccttt ctcaagaaaa  8340
acccaaacaa acaaaaaagt gaagccagtt ctttaatttc tattggagat atcacacacg  8400
ctccaaagag tggcaaaggt gaacattctt tggagctatt atatttctaa tgtaacatca  8460
atggccattt actcccaaag ggaaacatct tttttttttt tttttttaa gatggagtct  8520
ggctctgtca cccaggtggg agtgcaatgg caggatcttg gcccactgca acatcagcct  8580
cccaggttta agcaattctc ctgcatcagc ctccagagta gctgggatta caggtgcccg  8640
ccaccatggc tagctaaatt tttgtaattt ttagtagaga cagggtttta ccatgttggc  8700
caggccggtc tcgaacccct aacctcaagt gatccgcccg cctcaccctc cagaagtgct  8760
aggattacag gcctgagcca ccgcacccgg ccctgctatt tttttctatg tagttgtttc  8820
agtaatacca tatgagcaga gaatactatt gattcattca attgaagaaa tctgaataaa  8880
ttagtaaata taataattct tcaaaagagg accactttat gtttccaata gattatataa  8940
ttgaattcag gtaacgtaga gttattcaga cttttttttt taaataacgg aatttgcaa  9000
aaaaacaggt tgcatcgttt tctacagaga atattcagat gtgtagaggc aaagagactt  9060
tcttgaaagg tttttatttc ctgttaaatt tgtgaggaaa actcctgaga aaggaaagat  9120
ttacttttga aggaagaaag aacataaccc aaagaaattt gaaagattca aaaagagttt  9180
tccaaatgta ttctcatttc tttctcatat ttgttcaagg tcttagtttc caagcattca  9240
aaattaaatc ttgtttgcct aactcttcta acatctatta ccaacctaac atattacaat  9300
tctgtttaaa atgtgcagtt ctaaatgttc ttgcgtgcct cactgtggaa agtgtggtgc  9360
atggaactgc agcgtcagta tcacccagaa gtataattac aagaagtgca gagtccttgg  9420
ccttaccctg tacctacaga agtccgcttt tgggcaagat ccccagatga ttcatatgtg  9480
tattaatatt gaaaaaattg gaactagtaa gtcctagagg aggtaaattt taagggcttt  9540
ttaagggaac ttccaagtgt gaagacattt ctggagatga caagtcaaca tagcatggga  9600
tcttggctag acaaggaaag cgagagaaca ttaaataaac acaagcaacg acaaaccacc  9660
tatgttataa ttttatcctg gaccatccaa agtttactct tggtcacgct gtctaaccca  9720
gcctgcctcc tggcacttgc tagttagaac cagggaagag aaaactaata tgtgttaggt  9780
attataattt ccttatgtca cataaatttt ggtgccatag ctagcaatgt ttcttaatat  9840
cacatcagta caatgtgtcc attgccttct gtaacatttt taatgctatc aataatacat  9900
tgacattata aaaataaatg aatgtggtca ata                              9933

SEQ ID NO: 2           moltype = DNA  length = 3418
FEATURE                Location/Qualifiers
source                 1..3418
                       mol_type = genomic DNA
                       organism = Homo sapiens
SEQUENCE: 2
gaacggggag tgcaggcggg agcttttcga gacgccgccc cgggaacaca aggtgtcctt  60
ctccaccgaa cctccgcggg ggtcctcccc ggggaaagac accgaggatg gcgaggccgg  120
agaaggggat cctcggtccg gctttatgca gcgccagctt tctgccatgc ttcaacccgg  180
ggtcaacaag ttctcccttc ggatgttcgg gagcgagaaa gcggtggaga gggagcagga  240
gagggtgaaa tccgcggggg cctggatcat acacccgtac agtgacttca ggttttattg  300
ggatttcaca atgctgctct ttatggttgg gaacctaatt atcattcctg tgggaatcac  360
tttcttcaaa gaggaaacta ccataccatg gatcatattt aatgtggtgt cagacacctt  420
ctttcttatg gacttggttc tgaacttccg aactggtatc attattgagg acaacactga  480
gattatcttg gatccacaga agatcaagcg caaatatctg cgcacatggt tcgtggtgga  540
ctttgtgtcc tccatccctg tggattacat atttctcatt gtagaaaagg gcattgactc  600
tgaagtttat aagacggccc gtgctttaag aattgtgagg tttaccaaga tcctcagcct  660
cctgaggtta cttcgacttt ccagactcat tcggtatatt catcaatggg aagagatctt  720
ccacatgacc tatgacctgg ccagcgcagt gatgagaatt tttaacctga ttgccatgat  780
gctactgctt tgtcactggg atggatgtct tcagttcctg gttccaatgc tccaagactt  840
ccccagtaat tgttgggttt ccatcaacaa gatggtgaat gactcgtgga gtgaactgta  900
ctccttcgcc ctgttcaagg ccatgagcca catgctgtgc attggttacg ggcgccaggc  960
cccagaaagc atgactgata tctggcttac aatgttgagc atgatagtgg gcgctacatg  1020
ctacgccatg ttcattggac atgccacagc tctcatccag tcactggact catcccgcag  1080
acagtaccaa gaaaagtaca agcaagttga gcagtacatg tcctttcata agctgcctgc  1140
cgattttcgt caaaggcttc atgactatta cgaacatcgt taccagggga agatgtttga  1200
tgaagacagt atccttgaag agctaaatga gcctttgaga gaggaaatag tgaacttcaa  1260
ctgccgcaag ctggtagcat caatgccact ctttgccaat gctgatccct gcttcgttac  1320
ggcaatgctg accaaactaa aatttgaggt gttccagccc acggattaca tcattcggga  1380
gggaaccatc ggcaagaaga tgtacttcat ccagcatggt gttgtcagcg tacttaccaa  1440
gggcaacaag gaggtgaagc tctcggatgg ctcctacttt ggagagatct gcctgctgac  1500
acgggggcga cggactgcca gtgtccgcgc cgacacatac tgccgtctct actcactctc  1560
tgtggataat ttcaatgagg tgttggagga atacccaatg atgcggcgtg catttgagac  1620
ggttgccata gacagactgg atagaatagg gaagaagaat tccatcctca tgcacaaggt  1680
tcaacatgac ttgaactcag gtgtcttcaa caaccaggag aatgaaataa tacaagagat  1740
tgtcaagtat gatcgggaga tggtgcagca agctgagctc catcaacacc aactaagcgg  1800
tgggatgtat gccacatgca atcctccctc tcctcaaccc caggtcccat ctgccatagc  1860
aactttgcag caagctgtgg ccatgagctt ttgtccccca atggccagcc cactagtggg  1920
```

ttccccgcgt ataatgaggc gactccaata tgcccaagga gggcctggag ctttttctat 1980
atccccagct cttttccagc catccctgca gctcttgcag catcatccac ccccccagca 2040
ggttccacgt aggccatcca ctgctgtgcc cagtcccccc aaccaatcac cacgagtgtc 2100
tcagaacttt gcctacccag ccaggcctcg ggcaggctca caactttctc ttacccaatc 2160
tgggggttct ggttccccac aacgtctgtc tgtccacaag agcactcatt ctctgcactc 2220
tggcacactc acgcgtgagt ctcgacccct ttcagcctca cagccctcac tgcctcaggg 2280
ggcgtcacag ctccgcagtc caccagctcc tcctgctaca actggcagct taacctctcc 2340
ggtggccaaa ggaggtttgg gaccacaggc tggtccaaga gtacctgccc ctgcaagact 2400
tgcgctctcc catcagttgt cctcttctgg tacagttggt ggtgtctcgg actctgcagt 2460
agggacatcg ttaggaggca ggaaagattc tgtggttagt gccccagatt ctgaccctgt 2520
taggggacgg ctgtctgcaa acttgtgact gatgggtgta cacgttccct cactcaaatg 2580
ggtaggtaat ggatggtgca cagttgttat taagatagaa aatataatgt gccctcctag 2640
ccatctctgt gccactttat taataactct acttgtttaa agattagtag ccataccttt 2700
cctctggagt gggggtatta atatgtggaa gttacaagag aactagcagt tagatcagta 2760
aatgccactt cagaaagcaa tccgccacat aactcctcca gtgtttacaa aagtaggaaa 2820
atgcagcact gttcaatgtc acagatctac ctagagctct gcattgaaat gaagaagagt 2880
gcaaatcttc tgagggtcta aggcagctgg tctgctgtca gaaggaaaga gactgctggt 2940
atttactact gagttttttt ttagttattt aaattatata tatatatata cacacatatc 3000
aaaaactctt tcgctggtag atcctcactc tgaattcgca aattgaaaaa gctacaacga 3060
atattactta tgcccaaagc aagccaattt cgttatgcaa actgcaggca gtttgaccta 3120
gctattggtc ctttccagga ctttaactac ccagtgacag tgtcacctat ggatgtcatg 3180
ataagcacct atatttatat aaccatgcat acatttattt tagtttgtaa tcatgtttta 3240
tttaggagga ggtaaatttt tttgtgttat gtcaccattt gtgcccccat ttcctttcag 3300
tgagcaaatc accaactgaa tatagggatt caaattaggc actgcaagtc ccagtgacac 3360
actacatact attaattgta ttgacagcag taacactgca tgtggctgtt gtaaaaaa 3418

SEQ ID NO: 3 moltype = DNA length = 3732
FEATURE Location/Qualifiers
source 1..3732
mol_type = genomic DNA
organism = Homo sapiens
SEQUENCE: 3
catggaggcg gagcagaggc cgacgactag ggccagcgat ggggcgaccc ctgggctgga 60
gagggcgcct cctgctgccc cggcgtctac aaccacggcc tcggatccga ttcctgggtc 120
caggcccggg accgggcccg agcccaagag gaggcagctc gggacgctgc tccagcccac 180
ggtcaacaag ttctcccttc gcgtgttcgg cagccacaaa gcagtggaaa tcgagcagga 240
gcgggtcaag tcagcggggg cctggatcat ccacccctac agcgacttcc ggttttactg 300
ggacctgatc atgctcctgc tgatggtggg gaacctcatt gtgctacctg tgggcatcac 360
cttcttcaag gaggagaact ccccaccttg gatcgtcttc aacgtcctct ctgacacttt 420
cttcctgatg gatctggtgc tcaacttccg cacaggcatc gtggtagagg agggtgctga 480
gatcctgctg gcaccgcggg ccatccgcac acgctacctg cgcacctggt tcctggttga 540
tcttatctcc tctattcctg tggattacat tttcctggtg gtggagctgg agccacgact 600
ggacaccgag gtctacaaaa cagctcgggc cctgcgcatc gtgcgtttca ccaagatcct 660
cagcctgctg cggctgctcc gcctttcccg cctcatccgc tacatacacc agtgggagga 720
gatctttcac atgacctatg acctggccag tgctgtggtt cgcatcttca acctcatcgg 780
aatgatgctg ctgctatgtc actgggatgg ctgtctgcag ttcctggtcc ccatgctgca 840
ggacttccct cccgactgct gggtctccat caaccatatg gtgaactact cgtggggccg 900
ccagtattcc cacgccctgt tcaaggccat gagccacatg ctctgcattg gctacgggca 960
gcaggcacct gtgggcatgc ccgacgtctg gctcaccatg ctcagcatga tcgtgggtgc 1020
cacgtgctac gccatgttca tcggccacgc cactgccctc atccagtccc tggactcttc 1080
tcggcgtcag taccaggaga agtacaagca ggtggagcag tatatgtcct tccacaagct 1140
gccagctgac acacggcagc gcatccatga gtactatgag caccgctacc agggcaagat 1200
gtttgacgag gaaagcatcc taggagagct gagcgaacca cttcgggagg agatcattaa 1260
cttcacctgc cggggcctcg tggcccacat gccactgttc gcccacgccg accccagctt 1320
cgtcacggcc gtgctcacca agctacgctt tgaggtcttc cagccggggg acctcgtggt 1380
gcgtgagggc tccgtgggca ggaagatgta cttcatccag catgggctgc tcagtgtgct 1440
ggcacgtggc gcccgggaca cccgcctcac tgatggatca tactttgggg aaatctgtct 1500
gctgactcgg ggccgacgca cagccagtgt gcgtgctgac acctactgcc gcctctactc 1560
gctcagcgtg gaccatttca acgccgtgct cgaggagttc cccatgatgc gccgggcctt 1620
cgagacagtg gccatggatc ggctgcgccg cattggcaag aagaattcca tactgcagcg 1680
gaagcgctct gagccaagtc caggcagcag tgggggcatc atggagcagc acttggtgca 1740
acacgacagg gatatggctc ggggtgttcg gggcctggcc ccaggcacag gagctcggct 1800
cagcggaaag ccggtgctgt gggagccact agtgcacgca cccctgcaag cagccgccgt 1860
gacctccaat gtggccattg ccctgacgca ccagcggggc cctctccccc tctcccctga 1920
ctctccagtc accctccttg ctcgctctgc tcgaagatca gcaggagcag gctccccagc 1980
ctccccactt gtccctgtcc gagccggccc tctgctggcc cggggaccct gggcatccac 2040
ttcccgcctg ccggccccac ctgcccgaac cctccatgcc agcctatccc gggctgggcg 2100
ctcccaggtg tcactgctgg ggcctccccc aggaggaggt ggacggcgac taggacctcg 2160
gggccgccca ctctcagcct cccagccctc tctgcctcag cgggcagcag gtgatggctc 2220
tcctgggtgt aagggctcag gaggtgaacg cctgcccccc tcagggctcc tggctaagcc 2280
tccagggaca gcccagcccc ccaggccatc agtgcctgag ccagccactc cccggggccc 2340
ccaactctct tccaacatgt gaaacctttg ggtaagctct tgggtgccat agcatgtgcc 2400
agagggcaga cgcctcttgg ggacaccaag gggacctgaa acactgctct atgggagtat 2460
ctccccttag taccaagaag atggtctctg ttctcagctc aggcgccttg caacctgaca 2520
tcctcctaat ccattcaccc attcatcaaa gatacttagc gcctaccatg ttcaaggcac 2580
tgtaccagac gctgtatgtc tccactgcca agtagaagtg actccaagcc ctctgatgag 2640
ggtattcccc tagccatggt cctgccaggt gcaggcctgg gcccatgatc ccatcttact 2700
aagcacaagt acttgccacc accatcactg ccaagtaact agatgtctct gttttcctgc 2760
ccatgacctt gcaggttctg cctggcatgg ttatcttcct gtccgctagc atagctgggc 2820

-continued actgccaatt acctgtcccc ccgctgctgt caacaaatgt cttgggtccc tggtgtgggc 2880
atccagcttt actgccatgc gtggaccctc cctgtctata ccccccgagt gggaacacac 2940
atctcctgac aagttccttg cactctctgt ctctgtgata gaactgcctt tttgtaaact 3000
gagagccacc tcctccctat gcccctgtcc cagggacaac cccccttgaag ctaagggatt 3060
gttgacaccc ccttatttag tgtgccagcg tagattcccc ccaggttggg ggcaagtgaa 3120
tccttagatg gaattttttc tttccttgct cccttcctta tttattcaat catttaataa 3180
ttgtatttat tcactcattt gctagtttta tttattatca attcatttta tttgtccatt 3240
catttatcca tctctcccat cccctcctgg tagggagaca ggaatgggca gagcccctcc 3300
atgccagctc ttgtggtcct tgcgcaactc ccgtcagtgg caattcttga gccctctccc 3360
taactaggta ggagcaggaa ggccacctga gagggagagg aggactgttc ttatttttag 3420
gcttttttttc ctttctactg agtttgctgc tggtgcagga gtaaggggag ggcccgaggt 3480
aaccaagcct ggggaagggc aggctagcca gtacctctgc cttctcaggg acaagagaag 3540
cccccctatcc cacccctctg tccccacacc tactctacag catcagagaa tgaggggcca 3600
ggaccctaaa tctcctttc tcctgggtgg gcagttctgg ggttctgggt gtgtgggaga 3660
ggttttatat tgcttccaaa cacctgggtt taaaaagaaa atagagacac ttgttttggc 3720
tcctggcttg tg 3732

SEQ ID NO: 4 moltype = DNA length = 7476
FEATURE Location/Qualifiers
source 1..7476
mol_type = genomic DNA
organism = Homo sapiens
SEQUENCE: 4
gtcccacccg cgcgccctgt gcgtgtctcc ctgtttcccc acgccctcct tgcctggctg 60
ctgcgaggct ttgcagggga aagactggcg cggggttcgc cccctgccca tgtcacagga 120
aaaccctggg agcctccccg acgcggcgca tttccggaaa cccctcccca agcgggttgc 180
gggaaggccg ggactctgca tccagaagac ccggtcgcct cccaaaagga agagtcggag 240
acccagctga ggggcaaaca tgccagggaa aggcgagccc agagcttggt gatggagaat 300
ttgggaagcc accccgcccc cttcaatctt gggatgggga attcgcaact gaagccggag 360
ctctagactt ggggcgcgct cccagcttgg cccaagaaag agatttaagg gcgcagcagt 420
atggacacct ctcaccccgg ctccgaaggt ctagcgaggg tctaacccgg gcccctcgcc 480
aggcccgccc cccgcccccc gccccctccc agcccccggc ccgtgcgccg ctgccccttt 540
aagaagccca ggtaggcagg ccgggctgcg ggagccgctc ctatggcaac ccgcgagctg 600
cggcggcttc atgaatattc cggggcgcgg gagcccgagc gcggccggag ggcgctccgg 660
gggaggcggc cgctgatgta agcccggcgg gtcgctgggc tccgctcggc tgcggcggga 720
gccccgggac gggccagagg ggccgggcca gaggaggcga gacgaggtcg caggggggcca 780
gccacaaagt ccgggcggcg agacagacgg acggccagcc ctcccgcggg acgcacgccc 840
gggacccgcg cgggccgtgc gctctgcgct ccggagcggt tccccgagcg ccgcggccgc 900
agagcctctc cagccggcgc ccattgttcc ccgcgggggc ggggcgcctg gagccgggcc 960
gcgcgccgcg cccctgaacg ccagagggag ggagggaggg agggaggcaa ggagggagcg 1020
cggagtccga gcgcccagcc cgggaggagg cgcagcgcgg cgagcccggg gagtcggagc 1080
gcaactggga gcctcccagc ggcgcacagc ctgcccgagc atgggcgcct gaggcggccc 1140
cacgccggcg gcgaaggacg agtccccacg ggcggactga ctggcgggcg gacctggagc 1200
ccgtccgcgg cgccgcgccc ctatccccgg cccggtccgg ccccggcccc tggcgccatg 1260
gacaagctgc caccgtccat gcgcaagcgg ctctacagtc tcccgcagca ggtgggggcc 1320
aaggcgtgga tcatggacga ggaagaggac gccgaggagg aggggggcgg gggccgccaa 1380
gaccccagcc gcaggagcat ccggctgcgg ccactgccct cgccctcgcc ctcgccctcg 1440
gcggccgcgg gtggtacgga gtcccggagc tcggccctcg ggcagcggca cagcgaaggg 1500
ccggcccgcg gcgcgggcaa gtccagcacg aacggcgact gcaggcgctt ccgcgggagc 1560
ctggcctcgc tgggcagccg gggcggcggc ggcagcggca cggggagcgg cagcagtcac 1620
ggacacctgc atgactccgc ggaggagcgg cggctcatca ccgagggcga cgcgtccccc 1680
ggcgaggaca ggacgccccc aggcctggcg gccgagcccg agcgccccgg cgcctcagcg 1740
cagcccgcag cctcgccgcc gccgccccag cagccaccgc agccgacctc ctcctcctgc 1800
gagcagccct cagcggacac cgctatcaaa gtggagggag gcgcggccac cggcgaccag 1860
atccttccgg aggccgaggt gcgcttgggc cagtccggtt tcatgcagcg ccagttcggg 1920
gccatgctcc aacccggggt gaacaaattc tccctaagga tgttcggcag ccagaaagcc 1980
gtggaacgcg agcaggagag ggtcaagtcg gccggatttt ggattatcca cccctacagt 2040
gacttcagat tttactggga cctgaccatg ctgctgctga tggtgggaaa cctgatcatc 2100
attcctgtgg gcatcacctt cttcaaggat gagaacacca caccctggat tgtcttcaat 2160
gtggtgtcag acacattctt cctcatcgac ttggtcctca acttccgcac agggatcgtg 2220
gtggaggaca acacagagat catcctggac ccgcagcgga ttaaaatgaa gtacctgaaa 2280
agctggttca tggtagattt catttcctcc atccccgtgg actacatctt cctcattgtg 2340
gagacacgca ttgactcaga ggtctacaag actgcccggg ccctgcgcat cgtccgcttc 2400
acgaagatcc tcagcctctt acgcctatta cgcctctccc gcctcattcg atatattcac 2460
cagtgggaag agatcttcca catgacctac gacctggcca gcgccgtggt gcgcatcgtg 2520
aacctcatcg gcatgatgct cctgctctgc cactgggatg gctgcctgca gttcctggta 2580
cccatgctgc aggacttccc tgatgactgc tgggtgtcca tcaacaacat ggtgaacaac 2640
tcctggggga agcagtactc ctacgcgctc ttcaaggcca tgagccacat gctgtgcatc 2700
ggctatggac ggcaggcgcc cgtgggcatg tccgacgtct ggctcaccat gctcagcatg 2760
atcgtgggcg ccacctgcta cgccatgttc attggccacg ccactgccct catccagtcc 2820
ctggactcct cccggcgcca gtaccaggaa aagtataagc aggtggagca gtacatgtcc 2880
ttccacaagc tcccgcccga cacccggcag cgcatccacg actactacga gcaccgctac 2940
cagggcaaga tgttcgatga ggagagcatc ctgggcgagc tgagcgagcc cctgcgggag 3000
gagatcatca actttaactg ccggaaactg gtggcctcca tgccactgtt tgccaacgcg 3060
gaccccaact ttgtgacgtc catgctgacc aagctgcgtt tcgaggtctt ccagcctggg 3120
gactacatca tccgggaagg caccatcggc aagaagatgt acttcattca gcacggcgtg 3180
gtcagcgtgc tcaccaaggg caacaaggag accaagctgg ccgacggctc ctactttgga 3240
gagatctgcc tgctgacacg gggccggcgc acagccagcg tgagggccga cacctactgc 3300
cgcctctact cgctgagcgt ggacaacttc aatgaggtgc tggaggagta ccccatgatg 3360

```
cgaagggcct ttgagactgt ggcgctggac cgcctggacc gcatcggcaa gaagaactcc  3420
atcctcctcc acaaagtcca gcacgacctc aactcgggcg tcttcaacta ccaggagaac  3480
gagatcatcc agcagattgt gcagcatgac cgggagatgg cgcactgcgc acaccgcgtc  3540
caggccgccg cctctgccac cccgaccccc acacctgtca tctggacccc gctgatacag  3600
gcaccactgc aggctgccgc tgccaccact tctgtggcca tagccctcac ccaccaccct  3660
cgcctgcctg ctgccatctt ccgccctccc ccaggatctg ggctgggcaa cctcggtgcc  3720
gggcagacac caaggcacct gaaacggctg cagtccctga tcccttctgc gctgggctcc  3780
gcctcacccg ccagcagccc atcccaggta gacacgccgt cttcatcctc cttccacatc  3840
caacagctgg ctggattctc tgcccccgcc ggactgagcc cactcctgcc ctcatcgagc  3900
tcctccccac cccccggggc ctgtggctcc ccctcggctc ccacaccatc agctggcaca  3960
gccgccacca ccacagccgg gtttggccac ttccacaagg cactgggtgg ctccctgtcc  4020
tcctccgact ctcccctgct caccccgctg cagccaggtg cccgctcccc gcaggctgcc  4080
caaccacctc ccgcaccacc cggggcccgg ggaggcctgg gactcccgga gcacttcctg  4140
ccacccccac cctcatccag atccccatca tctagccctg ggcagctggg ccagcctccc  4200
ggggagttgt ccctaggtct agctgctggc ccaccgagca cgccagagac acccccacgg  4260
cagcctgagc cgccatccct tgtggcaggg gcctctgggg gggcttcccc tgtaggcttt  4320
actccccgag gaggtctcag ccccccctggc cacagcccag gccccccaag aaccttccca  4380
agtgccccgc cccgggcctc tggctcccac ggatccttgc ttctgccacc tgcatccagc  4440
cccccaccac cccaggtccc ccagcgcagg ggcacgcccc ccctcacccc cggccgcctc  4500
acccaggacc tcaagctcat ctctgcatct cagccagccc tgcctcaaga cggggcacag  4560
actctccgca gagcctcccc gcactcctca ggggagtcca tggctgcctt cccgctcttc  4620
cccagggctg ggggtggcag cgggggcagt gggagcagca ggggccttgg tccccctggg  4680
aggccctatg gtgccatccc tggccagcac gtcactctgc ctcggaagac atcctcaggt  4740
tctttgccac cccctctgtc tttgtttggg gcaagagcca cctcttctgg ggggccccct  4800
ctgactgctg gaccccagag ggaacctggg gccaggcctg agccagtgtg ctccaaactg  4860
ccgtccaatc tatgagctgg gcccttccct cttctttctt cttttctctc ccttccttct  4920
tccttcaggt ttaactgtga ttaggagata aaccaataac agtaataatt atttaaaaaa  4980
ccacacacac cagaaaatca aaagacagca gaaaataacc aggtattctt agagctatag  5040
atttttggtc acttgctttt atagactatt ttaatactca gcactagagg gagggagggg  5100
gagggaggag ggagcaggca ggtcccaaat gcaaaagcca gagaaaggca gatggggtct  5160
cggggctggg caggggtcgg ggtggccagt gttgggggtt cttagagcag atgtgtcatt  5220
gtgttcattt agagaaacag ctgccatcag ccccttagct gtaacttgga gctccactct  5280
gcccccagga aggggctgcc ctggggcgtg ccctggggag cctcagatgc ctgcgacctt  5340
gggagaaaag ggccagggcc ctgagggcct agcatttttt tctactgtaa acgtagcaag  5400
atctgtatat gaatatatgt atatgtatgt aagatgtgta tatgtatagc tatgtagcgc  5460
tctgtagagc catgtagata gccactcaca tgtgcgcaca cgtgtgcagt ctagtttatt  5520
cctatgttgc caggatgccc gggtcacctt acacccagca acccaccttg gcccgcaggc  5580
tgtgcactgc atggtctcgg gatgttctct ctccagtcct cagggaagag gaccccagga  5640
cttcgcagca ggccccctct ctcgtctcaa atccagtccc agcctgacct ctcaccacac  5700
ggaagtggaa gactcctttc ctaggcctc aggcacaccc tgccacctct ggggccatca  5760
gtttgcccat ctgtacagcg ggaggtgagg ggaacttctg tgtattgagt ctgctctgtg  5820
ccaagcactg gtttcgctct ttacacatgt tcactccttc agtttcacaa agaccatggg  5880
gtgggcactt tcattctccc gatttagcag atgaagaaac agttctgggt aatttctcca  5940
ccatcatgta actcggagtg gcagagtggg gactgatttg aggttcaaat ccacgcctgc  6000
ttgaggccca agtctgtgtt ccttccatca gaaaactgtt gagggagtct gaggtagatg  6060
gtccccaagc gtggtgcaga aggaagacac cagattttgg cagcagtcag gcctgggttt  6120
gaatcccagc cctaccactt cttagctgta tgatcttggg caagttatct gacttttctg  6180
tcacctcatt tgtaaaatgg aaatcattat ggtaccgcct cacaaggacc tatgaggacc  6240
agatgcgaaa aatctgtatg tgaaatgccc agcccagcgc ctggcacata ccatggtagg  6300
tgctcaatca atcacatttc ttctgcccct catatgccca gcctattgct ccagcaaact  6360
atgtgagagc ccagggagct ttggctgagg gctccaagac ttaaaatctc aggactcagg  6420
aggtggctgg gcctccctaa gggcccaagg aaggtgtgtg gccagaggtg ggtgggagcc  6480
aggccttgag atgtgggaag acttcaacag ggagagaggg agggaatggt gggtgggatg  6540
gagtatatag cggagacatt cctgaggtgg atgtggagtg gtggatcagg gctttgggag  6600
ggaatccgca ggctgagggg tcagagggat ggccttgggt gataggctaa gggattgact  6660
gggcttggtc ctggcaacta ggagccataa gcaggttcca gattgcagga acgagaaagc  6720
agctcagatg cctttggagg caccatcctc cctcctccca gatgggatcc tgccagaggc  6780
aaagtcaggg gtctgcccct gcctataggg ccagggcagg tatagctgca atccccaaat  6840
aatgagatgg gctggcccca cattatccgt ccagaacatt ccatgcttca agccagaatg  6900
ttggcaagat cgagttttgc cttgagctat cctgggatgt gggaaaaacc gatttctcca  6960
tagatgggct gcagggagtg ggaggcggta ctccaggaga gaagtgggtg aaggttcctg  7020
ggatcttagg taaagactag atgccgcctg gtactggtct gtactgtgct ggctcaggag  7080
ttctgagaac tggaaggact tagcctcaac ctgagttctg cacacacccc ttccccttaa  7140
ggaaggcagc tctgagaggc agcaggactt gatccaaacc cacagtcttg tcctggaggc  7200
agcaggggtg aaggtggagg gtccagggcc gtgaggaggc tgcttgccat cagatcctgg  7260
cctaaccacc ctcttctgta cttacacaca catgtatttt ataatagctc tgacccaacc  7320
tggccactct gcagagactg ggacagccag gtgcaggcag tgggccctcc cacacccagt  7380
cacctacaag gaattttcaa atcttccact tttaaaaaag aaaccggtaa atgcgccgta  7440
ttgtatattt tatttaaata aaaaaaaatt ccagca                            7476

SEQ ID NO: 5           moltype = DNA  length = 20
FEATURE                Location/Qualifiers
source                 1..20
                       mol_type = other DNA
                       organism = synthetic construct
SEQUENCE: 5
gttcttagta ccactactgc                                              20

SEQ ID NO: 6           moltype = DNA  length = 20
```

-continued

```
FEATURE                 Location/Qualifiers
source                  1..20
                        mol_type = other DNA
                        organism = synthetic construct
SEQUENCE: 6
gtgcgcatcg tgaacctcat                                             20

SEQ ID NO: 7            moltype = DNA  length = 20
FEATURE                 Location/Qualifiers
source                  1..20
                        mol_type = other DNA
                        organism = synthetic construct
SEQUENCE: 7
agtacagttc actccacgag                                             20

SEQ ID NO: 8            moltype = DNA  length = 20
FEATURE                 Location/Qualifiers
source                  1..20
                        mol_type = other DNA
                        organism = synthetic construct
SEQUENCE: 8
atgtcactgg gatggctgtc                                             20
```